United States Patent
Billadeau et al.

(10) Patent No.: US 10,955,412 B2
(45) Date of Patent: Mar. 23, 2021

(54) GRAPHENE-MODIFIED ELECTRODES

(71) Applicant: MESO SCALE TECHNOLOGIES, LLC., Rockville, MD (US)

(72) Inventors: Mark Billadeau, Middletown, MD (US); Paul Freese, White Plains, MD (US); Alan Kishbaugh, Germantown, MD (US); Gisbert Spieles, Bethesda, MD (US); Nicholas Fox-Lyon, Bethesda, MD (US)

(73) Assignee: MESO SCALE TECHNOLOGIES, LLC., Rockville, MD (US)

( * ) Notice: Subject to any disclaimer, the term of this patent is extended or adjusted under 35 U.S.C. 154(b) by 746 days.

(21) Appl. No.: 15/309,944

(22) PCT Filed: May 8, 2015

(86) PCT No.: PCT/US2015/029804
§ 371 (c)(1),
(2) Date: Nov. 9, 2016

(87) PCT Pub. No.: WO2015/171971
PCT Pub. Date: Nov. 12, 2015

(65) Prior Publication Data
US 2017/0241995 A1    Aug. 24, 2017

Related U.S. Application Data

(60) Provisional application No. 61/990,839, filed on May 9, 2014.

(51) Int. Cl.
*G01N 33/543* (2006.01)
*G01N 21/76* (2006.01)
(Continued)

(52) U.S. Cl.
CPC ........ *G01N 33/5438* (2013.01); *C12Q 1/001* (2013.01); *G01N 21/66* (2013.01);
(Continued)

(58) Field of Classification Search
CPC ....... G01N 33/5438; G01N 33/543893; G01N 21/66; G01N 21/69; G01N 21/76; C12Q 1/001
See application file for complete search history.

(56) References Cited

U.S. PATENT DOCUMENTS

| | | |
|---|---|---|
| 5,093,268 A | 3/1992 | Leventis et al. |
| 5,147,806 A | 9/1992 | Kamin et al. |

(Continued)

FOREIGN PATENT DOCUMENTS

| | | |
|---|---|---|
| EP | 2426487 A1 | 3/2012 |
| WO | WO 97/36931 A1 | 10/1997 |

(Continued)

OTHER PUBLICATIONS

Graphene in Electronics, Future Markets, Inc., Edition 1, Mar. 2014, p. 1-126 (http://www.nanotechmag.com/wp-content/uploads/2014/09/Graphene-in-Electronics2.pdf).*

(Continued)

*Primary Examiner* — Robert J Eom
(74) *Attorney, Agent, or Firm* — Scully, Scott, Murphy & Presser, P.C.

(57) ABSTRACT

The specification provides an assay electrode including a composite containing a matrix and a multiplicity of graphene particles dispersed therein.

29 Claims, 9 Drawing Sheets
(9 of 9 Drawing Sheet(s) Filed in Color)

(51) Int. Cl.
*C12Q 1/00* (2006.01)
*G01N 21/69* (2006.01)
*G01N 21/66* (2006.01)

(52) U.S. Cl.
CPC ............ *G01N 21/69* (2013.01); *G01N 21/76* (2013.01); *G01N 33/54393* (2013.01)

(56) References Cited

U.S. PATENT DOCUMENTS

| | | | |
|---|---|---|---|
| 5,238,808 | A | 8/1993 | Bard et al. |
| 5,240,863 | A | 8/1993 | Shibue et al. |
| 5,308,754 | A | 5/1994 | Kankare et al. |
| 5,324,457 | A | 6/1994 | Zhang et al. |
| 5,589,136 | A | 12/1996 | Northrup et al. |
| 5,591,581 | A | 1/1997 | Massey et al. |
| 5,597,910 | A | 1/1997 | Gudibande et al. |
| 5,641,623 | A | 6/1997 | Martin |
| 5,643,713 | A | 7/1997 | Liang et al. |
| 5,679,519 | A | 10/1997 | Oprandy |
| 5,705,402 | A | 1/1998 | Leland et al. |
| 5,731,147 | A | 3/1998 | Bard et al. |
| 5,776,672 | A | 7/1998 | Hashimoto et al. |
| 5,786,141 | A | 7/1998 | Bard et al. |
| 5,846,485 | A | 12/1998 | Leland et al. |
| 5,866,434 | A | 2/1999 | Massey et al. |
| 6,066,448 | A | 5/2000 | Wohlstadter et al. |
| 6,136,268 | A | 10/2000 | Ala-Kleme et al. |
| 6,140,045 | A | 10/2000 | Wohlstadter et al. |
| 6,207,369 | B1 | 3/2001 | Wohlstadter et al. |
| 7,497,997 | B2 | 3/2009 | Glezer et al. |
| 7,842,246 | B2 | 11/2010 | Wohlstadter et al. |
| 8,278,757 | B2 | 10/2012 | Crain et al. |
| 2004/0022677 | A1 | 2/2004 | Wohlstadter et al. |
| 2007/0092432 | A1 | 4/2007 | Prud'Homme et al. |
| 2011/0201099 | A1 | 8/2011 | Anderson et al. |
| 2012/0145234 | A1* | 6/2012 | Roy-Mayhew ...... H01G 9/2022 136/256 |
| 2012/0220053 | A1 | 8/2012 | Lee et al. |
| 2012/0255860 | A1* | 10/2012 | Briman ................ H01B 1/04 204/403.15 |
| 2013/0248380 | A1 | 9/2013 | Cui |

FOREIGN PATENT DOCUMENTS

| | | |
|---|---|---|
| WO | WO 98/12539 A1 | 3/1998 |
| WO | WO 98/57154 A1 | 12/1998 |
| WO | WO 99/14599 A1 | 3/1999 |
| WO | WO 99/32662 A1 | 7/1999 |
| WO | WO 99/58962 A1 | 11/1999 |
| WO | WO 99/63347 A1 | 12/1999 |
| WO | WO 00/03233 A1 | 1/2000 |
| WO | WO 2012/112746 A1 | 8/2012 |

OTHER PUBLICATIONS

Lee, Bong-Kee, Sung Jea Park, and Dong Sung Kim. "Fabrication of ionic polymer actuator with graphene nanocomposite electrodes and its characterization." Current Applied Physics 13.7 (2013): 1520-1524.*

Huang, Liang, Chun Li, and Gaoquan Shi. "High-performance and flexible electrochemical capacitors based on graphene/polymer composite films." Journal of Materials Chemistry A 2.4: 968-974. (Year: 2013).*

Liu, Qin, et al. "Electrochemical detection of dopamine in the presence of ascorbic acid using PVP/graphene modified electrodes." Talanta 97: 557-562. (Year: 2012).*

International Search Report dated Jul. 31, 2015 issued in PCT/US2015/029804.

* cited by examiner

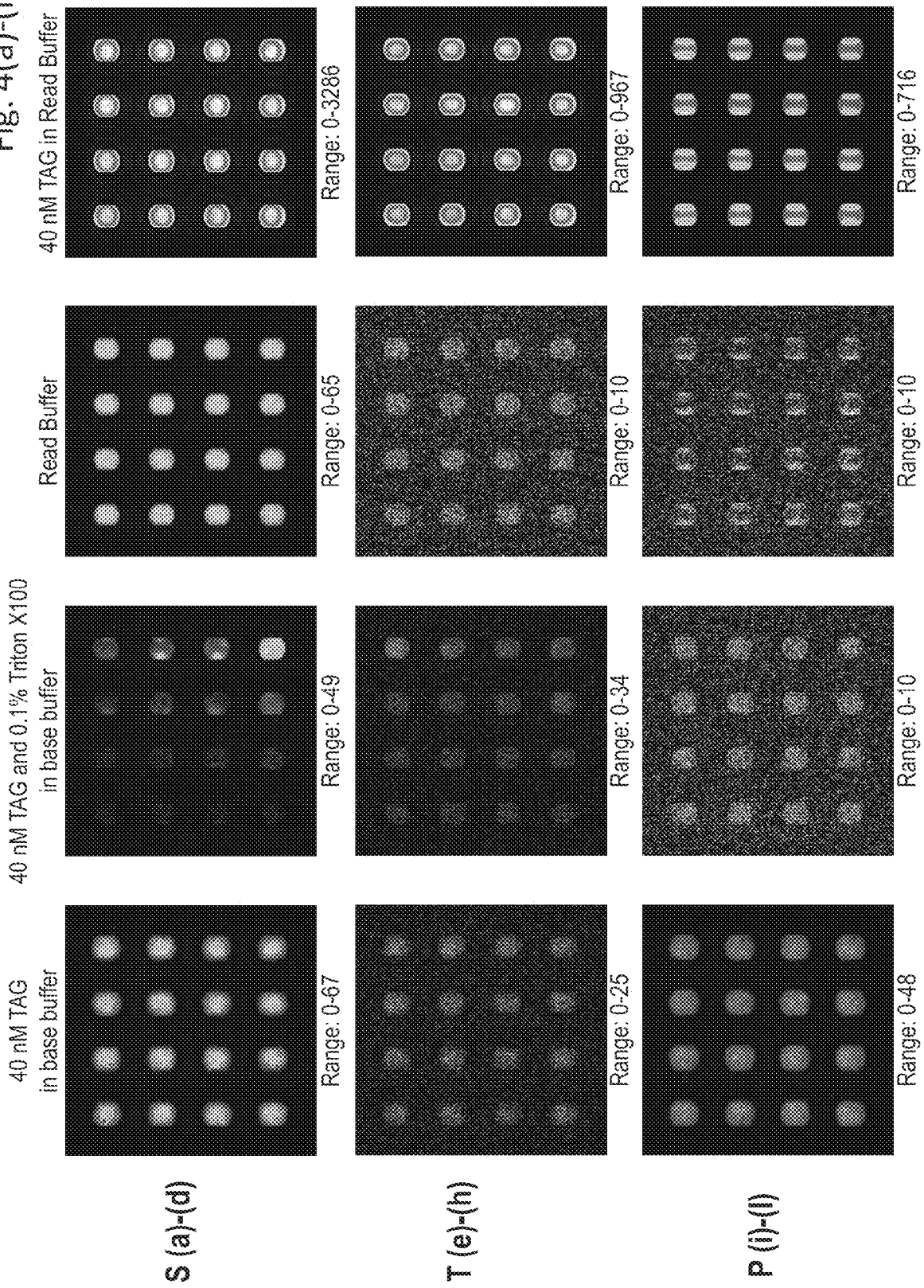

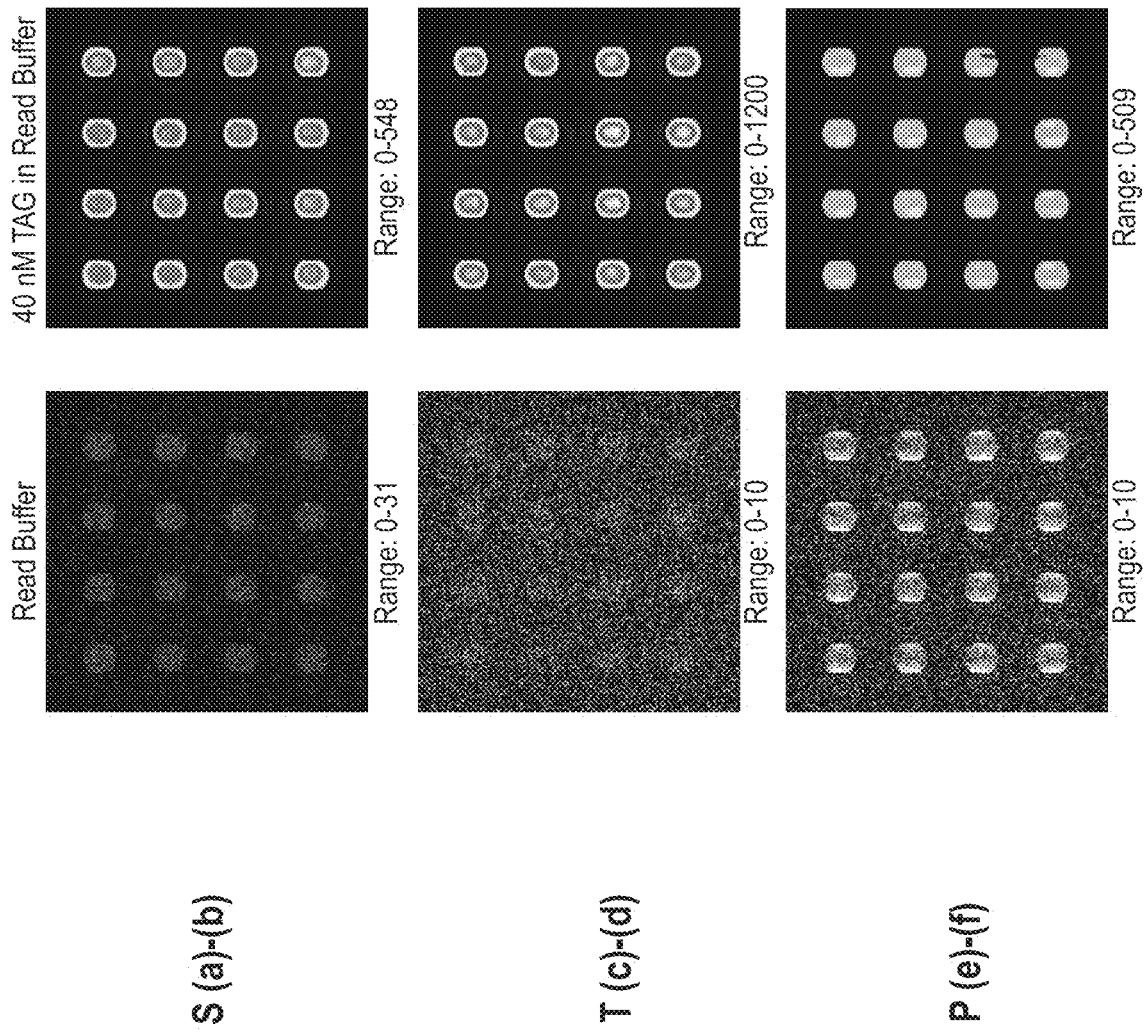
Fig. 5(a)-(f)

GRAPHENE-MODIFIED ELECTRODES

FIELD OF THE INVENTION

This application relates to graphene-modified electrodes and their use in plates, plate components, kits, apparatuses and methods for conducting chemical, biochemical and/or biological assays.

BACKGROUND OF THE INVENTION

At this time, there are a number of commercially available instruments that utilize electrochemiluminescence (ECL) for analytical measurements. Species that can be induced to emit ECL (ECL-active species) have been used as ECL labels. Examples of ECL labels include: i) organometallic compounds where the metal is from, for example, the noble metals of group VIII, including Ru-containing and Os-containing organometallic compounds such as the tris-bi-pyridyl-ruthenium (RuBpy) moiety and ii) luminol and related compounds. Species that participate with the ECL label in the ECL process are referred to herein as ECL coreactants. Commonly used coreactants include tertiary amines (e.g., see U.S. Pat. No. 5,846,485, herein incorporated by reference), oxalate, and persulfate for ECL from RuBpy and hydrogen peroxide for ECL from luminol (see, e.g., U.S. Pat. No. 5,240,863, herein incorporated by reference). The light generated by ECL labels can be used as a reporter signal in diagnostic procedures (Bard et al., U.S. Pat. No. 5,238,808, herein incorporated by reference). For instance, an ECL label can be covalently coupled to a binding agent such as an antibody or nucleic acid probe; the participation of the binding reagent in a binding interaction can be monitored by measuring ECL emitted from the ECL label. Alternatively, the ECL signal from an ECL-active compound may be indicative of the chemical environment (see, e.g., U.S. Pat. No. 5,641,623 which describes ECL assays that monitor the formation or destruction of ECL coreactants, herein incorporated by reference). For more background on ECL, ECL labels, ECL assays and instrumentation for conducting ECL assays see U.S. Pat. Nos. 5,093,268; 5,147,806; 5,324,457; 5,591,581; 5,597,910; 5,641,623; 5,643,713; 5,679,519; 5,705,402; 5,846,485; 5,866,434; 5,786,141; 5,731,147; 6,066,448; 6,136,268; 5,776,672; 5,308,754; 5,240,863; 6,207,369; and 5,589,136 and Published PCT Nos. WO99/63347; WO00/03233; WO99/58962; WO99/32662; WO99/14599; WO98/12539; WO97/36931 and WO98/57154, each of which are herein incorporated by reference.

Commercially available ECL instruments have demonstrated exceptional performance. They have become widely used for reasons including their excellent sensitivity, dynamic range, precision, and tolerance of complex sample matrices. The commercially available instrumentation uses flow cell-based designs with permanent reusable flow cells. The use of a permanent flow cell provides many advantages but also some limitations, for example, in assay throughput. In some applications, for example, the screening of chemical libraries for potential therapeutic drugs, assay instrumentation should perform large numbers of analyses at very high speeds on small quantities of samples. A variety of techniques have been developed for increasing assay throughput. The use of assay modules, e.g., multi-well assay plates and/or assay cartridges, allows for the parallel processing and analysis of multiple samples distributed in multiple wells or compartments of a plate. Multi-well assay plates and assay cartridges have been adapted to conduct chemical, biochemical and/or biological assays, including chemiluminescence, luminescence, and electrochemiluminescence assays, as described in U.S. application Ser. No. 10/185,274, now U.S. Pat. No. 7,842,246, U.S. application Ser. No. 08/814,085, now U.S. Pat. No. 6,140,045, and U.S. application Ser. No. 10/980,198, the disclosures of which are hereby incorporated by reference.

Assay modules configured to conduct electrochemiluminescence assays include integrated electrodes formed by screen printing a conductive ink on a substrate incorporated into the assay module, e.g., wherein the conductive ink comprises layers of carbon (see, e.g., U.S. application Ser. No. 10/185,274). Alternative conductive ink formulations suitable for use in assay modules configured to conduct biological or chemical assays are desirable, particularly those adapted to conduct electrochemiluminescence assays.

SUMMARY OF THE INVENTION

The invention provides an assay electrode comprising a composite containing a matrix and a multiplicity of graphene particles dispersed therein, said assay electrode having a binding domain containing a binding reagent, wherein said binding reagent is immobilized on a surface of said electrode. Specifically, the assay electrode includes a multiplicity of binding domains, and optionally, the binding reagent is selected from an antibody or fragment thereof, a nucleic acid, a receptor or an enzyme.

Also provided is a cartridge for use in an instrument system for conducting electrochemiluminescence assays for the detection or quantitation of an analyte, comprising: one or more electrodes as described herein and assay reagents.

Another embodiment of the invention is an apparatus for conducting an assay comprising: (a) an element including: (i) a matrix; and (ii) one or more graphene particles dispersed therein; and (b) binding reagents immobilized on said element to form one or more binding domains capable of binding a component of a binding assay.

A further embodiment is an apparatus for use in the detection of an analyte by electrochemiluminescence comprising: (a) an electrode including (i) a matrix; and (ii) one or more graphene particles dispersed therein; and (b) binding reagents immobilized on said electrode to form one or more binding domains containing a reagent capable of binding a component of an electrochemiluminescence assay.

Still further, the invention contemplates a cassette for use in the detection of analytes in a sample by electrochemiluminescence comprising: (a) a plurality of discrete binding domains on an electrode; and optionally, (b) a binding reagent comprising an electrochemiluminescence label; wherein said electrode comprises graphene.

Also provided is a multi-well plate comprising a plurality of wells, wherein two or more of said plurality of wells each comprise a working electrode surface and a counter electrode surface, wherein said working electrode surface and/or said counter electrode surface comprise graphene, e.g., screen printed graphene.

Another embodiment provided by the invention is a multi-well plate having a plurality of wells, wherein two or more of said plurality of wells each comprise a working electrode surface formed by applying one or more layers of graphene onto a conductive layer comprising silver.

Moreover, the invention includes an assay module comprising a substrate having one or more fluid channels for introducing samples and/or assay reagents and one or more working electrode surfaces and one or more counter electrode surfaces on said substrate, wherein said working electrode comprises a graphene ink.

Yet another embodiment is an assay module comprising a working electrode surface and a counter electrode surface, wherein said working electrode surface and said counter electrode surface comprise a printed conductive material comprising graphene.

A specific embodiment provides a multi-well plate comprising a plate top having plate top openings and a plate bottom mated to said plate top to define wells of said multi-well plate, said plate bottom comprising a substrate having a top surface with electrodes patterned thereon and a bottom surface with electrical contacts patterned thereon, wherein said electrodes and contacts are patterned to define two or more independently addressable sectors of two or more jointly addressable assay wells, each sector comprising two or more wells with: (a) jointly addressable working electrodes on said top surface of said substrate, wherein each of said working electrodes is electrically connected with each other and connected to at least a first of said electrical contacts; and (b) jointly addressable counter electrodes on said top surface of said substrate, wherein each of said counter electrodes is electrically connected with each other, but not with said working electrodes, and connected to at least a second of said electrical contacts, wherein said electrodes comprise graphene.

DESCRIPTION OF THE FIGURES

The file of this patent contains at least one drawing executed in color. Copies of this patent with color drawing(s) will be provided by the Patent and Trademark Office upon request and payment of the necessary fee.

FIGS. 4(a)-(l) are ECL images for electrodes comprising PF407C.

FIGS. 5(a)-(f) are ECL images for electrodes comprising X102 Vor-ink.

DETAILED DESCRIPTION OF THE INVENTION

Figure 1A:
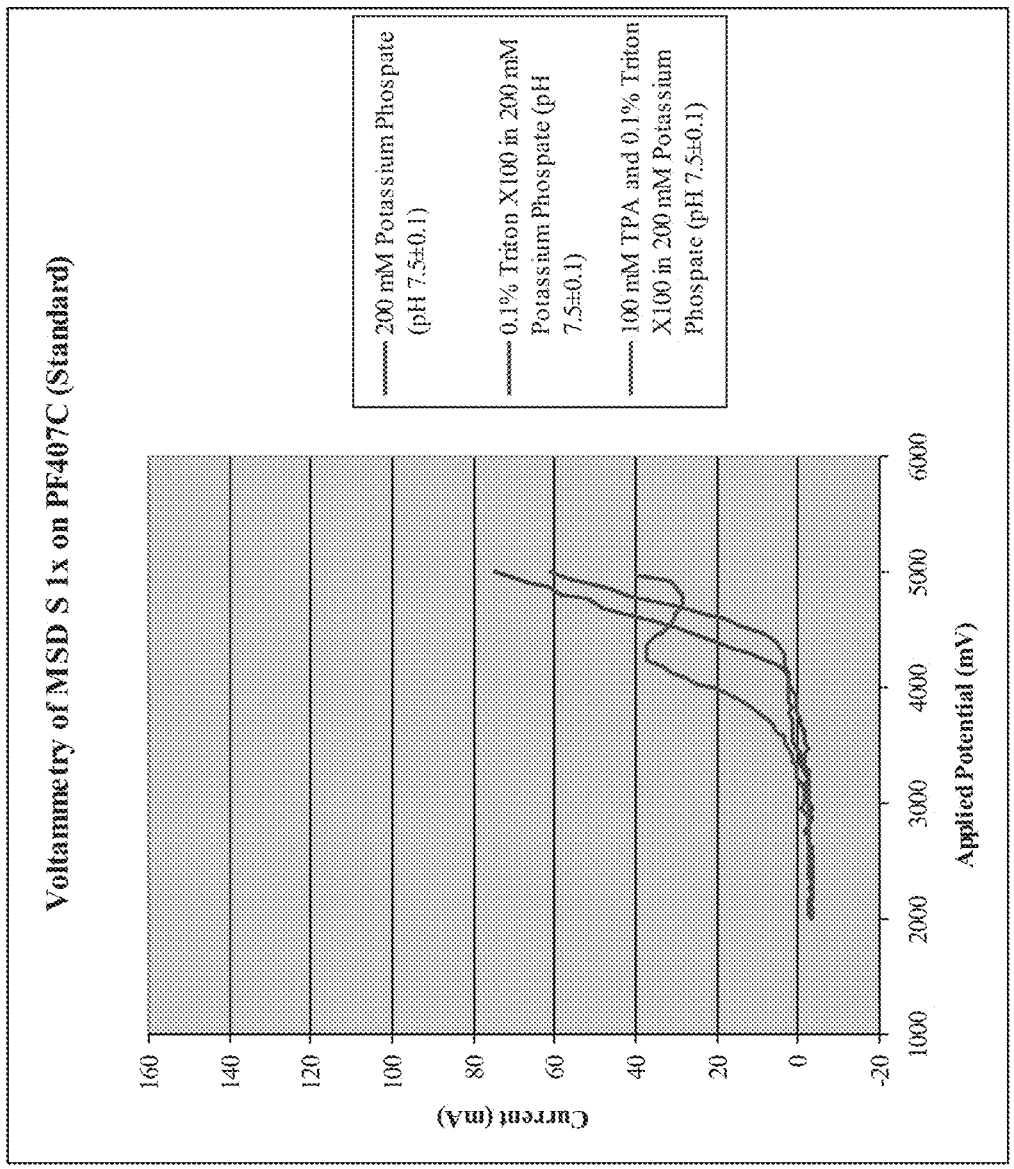
FIGS. 1(a)-(b) are graphs showing the voltammetry of S buffer using PF407C (panel (a)) and Vor-ink X102 (panel (b)), respectively.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

The invention relates to electrode compositions and surfaces and assay modules comprising those electrode compositions and surfaces. Electrode compositions of the present invention are comprised of a conductive material, e.g., copper, aluminum, a conductive alloy, or the like. They may also comprise oxide coated metals (e.g. aluminum oxide coated aluminum). Electrode surfaces can be working or counter electrodes and in one embodiment, working and counter electrodes do not comprise the same material (e.g. metal counter electrode and carbon working electrode). In a specific embodiment, electrode compositions include graphene and optionally, carbon-based materials such as carbon, carbon black, graphitic carbon, carbon nanotubes, carbon fibrils, graphite, carbon fibers, and mixtures thereof. Specifically, the electrode compositions comprise graphene. Advantageously, the electrode compositions may include conducting graphene-polymer composites, conducting particles dispersed in a matrix (e.g. graphene electrode compositions and/or a mixture of graphene and carbon inks), and/or conducting polymers.

One specific embodiment of the invention is an assay module, e.g., a multi-well plate, having electrodes (e.g., working and/or counter electrodes) comprising graphene, e.g., screen-printed layers of graphene inks. Some useful graphene inks include materials produced by Vorbeck Materials Corporation, Jessup, Md., e.g., graphene ink formulations described in U.S. Pat. No. 8,278,757, the disclosure of which is incorporated by reference in its entirety. A specific graphene ink formulation that can be used in the embodiments described herein is X102 Vor-ink, provided by Vorbeck Materials Corp.

In a specific embodiment, the electrode compositions include high surface area functionalized graphene sheets having a surface area of from about 300 to about 2630 $m^2/g$. The graphene sheets may comprise, in whole or in part, fully exfoliated, single sheets of graphene, or partially exfoliated graphene, in which two or more sheets of graphite have not been exfoliated from each other. Therefore, the graphene ink formulation may include mixtures of fully and partially exfoliated graphene sheets. One method of obtaining graphene sheets is from graphite and/or graphite oxide (also known as graphitic acid or graphene oxide). Graphite may be treated with oxidizing and intercalating agents and exfoliated. Graphite may also be treated with intercalating agents and electrochemically oxidized and exfoliated. Graphene sheets may be formed by ultrasonically exfoliating suspensions of graphite and/or graphite oxide in a liquid. Exfoliated graphite oxide dispersions or suspensions can be subsequently reduced to graphene sheets. Graphene sheets may also be formed by mechanical treatment (such as grinding or milling) to exfoliate graphite or graphite oxide (which would subsequently be reduced to graphene sheets). Reduction of graphite oxide to graphene may be by means of chemical reduction using hydrogen gas or other reducing agents. Examples of useful chemical reducing agents include, but are not limited to, hydrazines (such as hydrazine, N,N-dimethylhydrazine, etc.), sodium borohydride, hydroquinone, and the like. For example, a dispersion of exfoliated graphite oxide in a carrier (such as water, organic solvents, or a mixture of solvents) can be made using any suitable method (such as ultrasonication and/or mechanical grinding or milling) and reduced to graphene sheets.

In a specific method, graphite is oxidized to graphite oxide, which is then thermally exfoliated to form high surface area graphene sheets that are in the form of thermally exfoliated graphite oxide, as described in US 2007/0092432, the disclosure of which is hereby incorporated herein by reference. Thermally exfoliated graphite oxide formed by this method may display little or no signature corresponding to graphite or graphite oxide in its X-ray or electron diffraction patterns.

Graphite oxide may be produced by any method known in the art, such as by a process that involves oxidation of graphite using one or more chemical oxidizing agents and, optionally, intercalating agents such as sulfuric acid. Examples of oxidizing agents include nitric acid, sodium and potassium nitrates, perchlorates, hydrogen peroxide, sodium and potassium permanganates, phosphorus pentoxide, bisulfites, and the like. Preferred oxidants include $KClO_4$; $HNO_3$ and $KClO_3$; $KMnO_4$ and/or $NaMnO_4$; $KMnO_4$ and $NaNO_3$; $K_2S_2O_8$ and $P_2O_5$ and $KMnO_4$; $KMnO_4$ and $HNO_3$; and $HNO_3$. A preferred intercalation agent includes sulfuric acid. Graphite may also be treated with intercalating agents and electrochemically oxidized.

Exfoliation, including the exfoliation of graphite oxide, is preferably carried out at temperatures of at least 220° C. or more, preferably at temperatures of from 220 to 3000° C.

The graphene sheets used in the present invention have a surface area of from about 300 to about 2630 $m^2/g$, e.g., from about 350 to about 2400 $m^2/g$, or still more specifically of from about 400 to about 2400 $m^2/g$, or yet more specifically of from about 500 to about 2400 $m^2/g$. In another embodiment, the surface area is about 300 to about 1100 $m^2/g$. A single graphite sheet has a maximum calculated surface area of 2630 $m^2/g$. The surface area includes all values and subvalues therebetween, especially including 400, 500, 600, 700, 800, 900, 100, 110, 1200, 1300, 1400, 1500, 1600, 1700, 1800, 1900, 2000, 2100, 2200, 2300, 2400, and 2500 $m^2/g$.

The graphene sheets have a bulk density of from about 40 to about 0.1 $kg/m^3$. The bulk density includes all values and subvalues therebetween, especially including 0.5, 1, 5, 10, 15, 20, 25, 30, 35 $kg/m^3$. The graphene sheets typically have an overall carbon to oxygen molar ratio (C:O ratio), as determined by elemental analysis of at least about 1:1, or more specifically, at least about 3:2. Examples of carbon to oxygen ratios include about 3:2 to about 85:15; about 3:2 to about 20:1; about 3:2 to about 30:1; about 3:2 to about 40:1; about 3:2 to about 60:1; about 3:2 to about 80:1; about 3:2 to about 100:1; about 3:2 to about 200:1; about 3:2 to about 500:1; about 3:2 to about 1000:1; about 3:2 to greater than 1000:1; about 10:1 to about 30:1; about 80:1 to about 100:1; about 20:1 to about 100:1; about 20:1 to about 500:1; about 20:1 to about 1000:1. In some embodiments of the invention, the carbon to oxygen ratio is at least about 10:1, or at least about 20:1, or at least about 35:1, or at least about 50:1, or at least about 75:1, or at least about 100:1, or at least about 200:1, or at least about 300:1, or at least about 400:1, or at least 500:1, or at least about 750:1, or at least about 1000:1. The carbon to oxygen ratio also includes all values and subvalues between these ranges.

The average particle size of the graphene, carbon or graphite particle can vary over a wide range but, is typically in the range of from about 1 micron to about 50 microns, more specifically from about 2 microns to about 20 microns. If the average particle size of the graphene, carbon or graphite particles is less than about 1 micron, the electrical properties may be adversely affected. In other words, if the graphene, carbon or graphite particles are too fine, the resistivity of the composition may be too high. If the average particle size of the graphene, carbon or graphite particles is above about 50 microns, then the composition will be too difficult to apply to the substrate. For example, the composition will tend to clog up during a silk screening process or the like.

In a specific embodiment, the present invention provides an electrode composition comprising:

(a) a water soluble thermoplastic polymer in an amount of between about 0.25% and about 20% by weight;

(b) a polymer dispersion in water in an amount of between about 10% and about 70% by weight;

(c) a glycol drying-retarder agent(s) in an amount of between about 2% and about 20% by weight;

(d) an electrically conductive amount of graphene, alone or in suitable admixture with one or more additional conductive materials selected from carbon, graphite particles, or combinations thereof; and (e) water in a solvent effective amount, each of said amounts being based upon the total weight of said composition.

Examples of suitable thermoplastic water soluble polymers useful in the present invention include polyethyloxyazoline, polyvinyl pyrrolidone, polyvinyl alcohol, polyacrylamide, polyglycols and polyacrylic acid. Suitable binders can also include thermosets and/elastomers. Binders may also comprise monomers that can be polymerized before, during, or after the application of the ink to the substrate. Polymeric binders may be cross-linked or otherwise cured after the composition has been applied to the substrate. Examples of suitable polymeric binders include polyethers such as poly(ethylene oxide)s (also known as poly(ethylene glycol)s, poly(propylene oxide)s (also known as poly(propylene glycol)s, ethylene oxide/propylene oxide copolymers, cellulosic resins (such as ethyl cellulose, ethyl hydroxyethyl cellulose, carboxymethyl cellulose, cellulose acetate, cellulose acetate propionates, and cellulose acetate butyrates), and poly(vinyl butyral), polyvinyl alcohol and its derivatives, ethylene/vinyl acetate polymers, acrylic polymers and copolymers, styrene/acrylic copolymers, styrene/maleic anhydride copolymers, isobutylene/maleic anhydride copolymers, vinyl acetate/ethylene copolymers, ethylene/acrylic acid copolymers, polyolefins, polystyrenes, olefin and styrene copolymers, epoxy resins, acrylic latex polymers, polyester acrylate oligomers and polymers, polyester diol diacrylate polymers, UV-curable resins, and polyamide, including polyamide polymers and copolymers (i.e., polyamides having at least two different repeat units) having melting points between about 120 and 255° C. (such as those sold under the trade names Macromelt by Henkel and Versamid by Cognis).

Examples of suitable polymer dispersions in water include polyurethane, acrylic, polyester and vinyl resin polymers.

The purpose of the glycol drying retarding agent(s) employed in the present invention is to slow down the drying process so as to permit manipulation of the polymer thick film, such as by silk screening, before it has a chance to dry. Examples of suitable glycol type drying retarding agents include: diethylene glycol ethyl ether acetate; diethylene glycol butyl ether acetate; ethylene glycol butyl ether acetate; diethylene glycol monoethyl ether; ethylene glycol monoethyl ether; dipropylene glycol methyl ether; tripropylene glycol methyl ether; dibutyl phthalate; diocyl phthalate; diocyl phthalate; tributyl phosphate; 1,3 butylene glycol; propylene glycol and ethylene glycol. These agents may be used singularly or in combination with each other.

Other additional components may be added to the electrode composition. These include viscosity modifying agents and defoaming surfactants. The viscosity of the final conductive composition of this invention for screen printing is from about 8,000 to about 80,000 centipoises at 30° C. in order to be screen printable.

The electrode compositions of the present invention may optionally contain additional electrically conductive components other than the functionalized graphene sheets, such as metals (including metal alloys), conductive metal oxides, polymers, carbonaceous materials other than the high surface area functionalized graphene sheets, and metal-coated materials. These components can take a variety of forms, including particles, powders, flakes, foils, needles, etc. Examples of metals include, but are not limited to silver, copper, aluminum, platinum, palladium, nickel, chromium, gold, bronze, and the like. Examples of metal oxides include antimony tin oxide and indium tin oxide and materials such as fillers coated with metal oxides. Metal and metal-oxide coated materials include, but are not limited to metal coated carbon and graphite fibers, metal coated glass fibers, metal coated glass beads, metal coated ceramic materials (such as beads), and the like. These materials can be coated with a variety of metals, including nickel. Examples of electrically conductive polymers include, but are not limited to, polyacetylene, polyethylene dioxythiophene, polyaniline, polypyrrole, and the like. Examples of carbonaceous materials other than high surface area functionalized graphene sheets include, but are not limited to, carbon black, graphite, carbon nanotubes, vapor-grown carbon nanofibers, carbon fibers, metal coated carbon fibers.

The electrode compositions may optionally comprise one or more carriers in which some or all of the components are dissolved, suspended, or otherwise dispersed or carried. Examples of suitable carriers include, but are not limited to, water, distilled or synthetic isoparaffinic hydrocarbons (such Isopar® and Norpar® (both manufactured by Exxon) and Dowanol® (manufactured by Dow), citrus terpenes and mixtures containing citrus terpenes (such as Purogen, Electron, and Positron (all manufactured by Purogen)), limonene, aliphatic petroleum distillates, alcohols (such as methanol, ethanol, n-propanol, i-propanol, n-butanol, i-butanol, sec-butanol, tert-butanol, diacetone alcohol, butyl glycol, and the like), ketones (such as acetone, methyl ethyl ketone, cyclohexanone, i-butyl ketone, 2,6,8,trimethyl-4-nonanone and the like), esters (such as methyl acetate, ethyl acetate, n-propyl acetate, i-propyl acetate, n-butyl acetate, i-butyl acetate, carbitol acetate, and the like), glycol ethers (such as propylene glycol monomethyl ether and other propylene glycol ethers, ethylene glycol monobutyl ether and other ethylene glycol ethers, ethylene and propylene glycol ether acetates), N-methyl-2-pyrrolidone, and mixtures of two or more of the foregoing and mixtures of one or more of the foregoing with other carriers. Preferred solvents include low- or non-VOC solvents, non-hazardous air pollution solvents, and non-halogenated solvents.

The electrode compositions may optionally comprise one or more additional additives, such as dispersion aids (including surfactants, emulsifiers, and wetting aids), adhesion promoters, thickening agents (including clays), defoamers and antifoamers, biocides, additional fillers, flow enhancers, stabilizers, cross-linking and curing agents, and the like. In one embodiment of the present invention, the surfactant is at least one ethylene oxide/propylene oxide copolymer. The electrode compositions may also optionally comprise one or more prepolymers, oligomers, photo-initiators, and additional additives to allow for curing by UV, electron beam, or infra-red radiation. Examples of dispersing aids include glycol ethers (such as poly(ethylene oxide), block copolymers derived from ethylene oxide and propylene oxide (such as those sold under the trade name Pluronic® by BASF), acetylenic diols (such as 2,5,8,11-tetramethyl-6-dodecyn-5, 8-diol ethoxylate and others sold by Air Products under the trade names Surfynol® and Dynol®), salts of carboxylic acids (including alkali metal and ammonium salts), and polysiloxanes. Examples of grinding aids include stearates (such as Al, Ca, Mg, and Zn stearates) and acetylenic diols (such as those sold by Air Products under the trade names Surfynol® and Dynol®). Examples of adhesion promoters include titanium chelates and other titanium compounds such as titanium phosphate complexes (including butyl titanium phosphate), titanate esters, diisopropoxy titanium bis(ethyl-3-oxobutanoate, isopropoxy titanium acetylacetonate, and others sold by Johnson-Matthey Catalysts under the trade name Vertec. Examples of thickening agents include glycol ethers (such as poly(ethylene oxide), block copolymers derived from ethylene oxide and propylene oxide (such as those sold under the trade name Pluronic® by BASF).

The compositions of this invention may be applied to substrates by a variety of techniques, such as silk screening, spraying or brushing. Once the conductive polymer thick film has been applied to the substrates it is cured at about 93° C. sufficient to complete curing with good adhesion. The conductive compositions of the present invention may be applied to conventional rigid or flexible substrates. Whether the substrate is flexible or rigid in nature, the substrate may or may not have to be pre-treated or pre-coated with any other substance before applying the present composition.

The graphene sheets are present in the composition in at least about 0.01 weight percent based on the total weight of the ink. In one embodiment of the invention, the graphene sheets are present in the composition in at least about 0.01 weight percent, or more specifically in at least about 0.05 weight percent, or yet more specifically in at least about 0.1 weight percent, or still more specifically in at least about 0.5 weight percent, or even more specifically in at least about 1 weight percent, where the weight percentages are based on the total weight of the composition after it has been applied to the substrate and subjected to any post-application treatments (such drying, curing, cross-linking, etc.). However, as will be appreciated by those skilled in the art, the amount of graphene sheets present in the electrode compositions can be selected based on the desired electrical conductivity and the particular binders and other optional components chosen.

The electrode compositions may be made using any suitable method, including wet or dry methods and batch, semi-continuous, and continuous methods. For example, components of the electrode compositions, such as two or more of the functionalized graphene sheets, binders, carriers, and/or other components may be blended by using suitable mixing, dispersing, and/or compounding techniques and apparatus, including ultrasonic devices, high-shear mixers, two-roll mills, three-roll mills, cryogenic grinding crushers, extruders, kneaders, double planetary mixers, triple planetary mixers, high pressure homogenizers, ball mills, attrition equipment, sandmills, and horizontal and vertical wet grinding mills, and the like. The resulting blends may be further processed using wet or dry grinding technologies. The technologies can be continuous or discontinuous. Examples include ball mills, attrition equipment, sandmills, and horizontal and vertical wet grinding mills. Suitable materials for use as grinding media include metals, carbon steel, stainless steel, ceramics, stabilized ceramic media (such as yttrium stabilized zirconium oxide), PTFE, glass, tungsten carbide, and the like. After blending and/or grinding steps, additional components may be added to the electrode compositions, including, but not limited to, thickeners, viscosity modifiers, and the like. The electrode compositions may also be diluted by the addition of more carriers. After they have been printed on a substrate, the electrode compositions may be cured using any suitable technique, including drying and oven-drying (in air or another inert or reactive atmosphere), UV curing, IR curing, microwave curing or drying, and the like.

Electrodes may also include semiconducting materials (e.g. silicon, germanium) or semi-conducting films such as indium tin oxide (ITO), antimony tin oxide (ATO) and the like. Electrodes may also be comprised of mixtures of materials containing conducting composites, inks, pastes, polymer blends, metal/non-metal composites and the like. Such mixtures may include conductive or semi-conductive materials mixed with non-conductive materials. Preferably, electrode materials are substantially free of silicone-based materials. Electrodes may be formed into patterns by a molding process (i.e., during fabrication of the electrodes), by patterned deposition, by patterned printing, by selective etching, through a cutting process such as die cutting or laser drilling, and/or by techniques known in the art of electronics microfabrication (e.g., chemical etching, photopatterning of a resist material, microlithographic techniques, etc.).

Electrodes may be self-supporting or may be supported on another material, e.g. on films, plastic sheets, adhesive films, paper, backings, meshes, felts, fibrous materials, gels, solids (e.g. metals, ceramics, glasses), elastomers, liquids, tapes, adhesives, other electrodes, dielectric materials and the like. The support may be rigid or flexible, flat or deformed, transparent, translucent, opaque or reflective. Preferably, the support comprises a flat sheet of plastic such as acetate, polycarbonate, polypropylene, polyester (e.g., Mylar®), polyimide (e.g., Kapton®), or polystyrene. According to one embodiment, the material comprises polystyrene blended with High Impact Polystyrene (HIPS) to reduce the brittleness of the material. Preferably, between 4 and 16 wt % HIPS is blended with the polystyrene, more preferably between about 8 and 12 wt %. Electrode materials may be applied to a support by a variety of coating and deposition processes known in the art such as painting, spray-coating, screen-printing, ink jet printing, laser printing, spin-coating, evaporative coating, chemical vapor deposition, laminating, etc. Supported electrodes may be patterned using photolithographic techniques (e.g., established techniques in the microfabrication of electronics), by selective etching, and/or by selective deposition (e.g., by evaporative or CVD processes carried out through a mask). In a preferred embodiment, electrodes are comprised of extruded films of conducting carbon/polymer composites. In another preferred embodiment, electrodes are comprised of a screen printed conducting ink deposited on a substrate. Yet another embodiment involves the combination of a counterelectrode comprising a chemically etched metal (e.g., steel) or die-cut aluminized film and a screen-printed working electrode.

Electrodes may be supported by another conducting material. Advantageously, conducting carbon electrodes may be in contact with conducting metal pastes. Preferably, electrodes are (or are capable of being) derivatized or modified, for example, to immobilize assay reagents such as binding reagents on electrodes. One may attach, e.g., antibodies, fragments of antibodies, proteins, enzymes, enzyme substrates, inhibitors, cofactors, antigens, haptens, lipoproteins, liposaccharides, bacteria, cells, sub-cellular components, cell receptors, viruses, nucleic acids, antigens, lipids, glycoproteins, carbohydrates, peptides, amino acids, hormones, protein-binding ligands, pharmacological agents, and/or combinations thereof. It may also be desirable to attach non-biological entities such as, but not limited to polymers, elastomers, gels, coatings, ECL tags, redox active species (e.g., tripropylamine, oxalates), inorganic materials, chemical functional groups, chelating agents, linkers etc. Reagents may be immobilized on the electrodes by a variety of methods including passive adsorption, specific binding and/or through the formation of covalent bonds to functional groups present on the surface of the electrode.

Electrodes may be modified by chemical or mechanical treatment to improve the immobilization of reagents. The surface may be treated to introduce functional groups for immobilization of reagents or to enhance its adsorptive properties. Surface treatment may also be used to influence properties of the electrode surface, e.g., the spreading of water on the surface or the kinetics of electrochemical processes at the surface of the electrode. Techniques that may be used include exposure to electromagnetic radiation, ionizing radiation, plasmas or chemical reagents such as oxidizing agents, electrophiles, nucleophiles, reducing agents, strong acids, strong bases and/or combinations thereof. Treatments that etch one or more components of the electrodes may be particularly beneficial by increasing the roughness and therefore the surface area of the electrodes. In the case of composite electrodes having conductive particles or fibers (e.g., graphene, carbon particles or fibrils) in a polymeric matrix or binder, selective etching of the polymer may be used to expose the conductive particles or fibers.

One particularly useful embodiment is the modification of the electrode, and more broadly a material incorporated into the present invention by treatment with a plasma, specifically a low temperature plasma, also termed glow-discharge. The treatment is carried out in order to alter the surface characteristics of the electrode, which come in contact with the plasma during treatment. Plasma treatment may change, for example, the physical properties, chemical composition, or surface-chemical properties of the electrode. These changes may, for example, aid in the immobilization of reagents, reduce contaminants, improve adhesion to other materials, alter the wettability of the surface, facilitate deposition of materials, create patterns, and/or improve uniformity. Examples of useful plasmas include oxygen, nitrogen, argon, ammonia, hydrogen, fluorocarbons, water and combinations thereof. Oxygen plasmas are especially preferred for exposing carbon particles in carbon-polymer composite materials. Oxygen plasmas may also be used to introduce carboxylic acids or other oxidized carbon functionality into carbon or organic materials (these may be activated, e.g., as active esters or acyl chlorides) so as to allow for the coupling of reagents. Similarly, ammonia-containing plasmas may be used to introduce amino groups for use in coupling to assay reagents.

Treatment of electrode surfaces may be advantageous so as to improve or facilitate reagent immobilization, change the wetting properties of the electrode, increase surface area, increase the binding capacity for the immobilization of reagents or the binding of analytes, and/or alter the kinetics of electrochemical reactions at the electrode. In some applications, however, it may be preferable to use untreated electrodes. For example, we have found that it is advantageous to etch electrodes prior to adsorbing binding reagents (e.g., avidin, streptavidin or antibodies) when the application calls for a large dynamic range and therefore a high binding capacity per area of electrode. Oxidative etching (e.g., by oxygen plasma) can be advantageous in that the potential for oxidation of tripropyl amine (TPA) and the contact angle for water are both reduced relative to the unetched ink. The low contact angle for water allows reagents to be adsorbed on the electrode by application of the reagents in a small volume of aqueous buffer and allowing the small volume to spread evenly over the electrode surface. Assays may also be carried out on unetched electrodes despite the presence of polymeric binders in the ink. In fact, in some applications requiring high sensitivity or low non-specific binding it is preferred to use unetched electrodes so as to minimize the surface area of exposed surface and therefore minimize background signals and loss of reagents from non-specific binding of reagents to the exposed surface. Depending on the ink used and the process used to apply the ink, the electrode surface may not be easily wettable by aqueous solutions. We have found that we can compensate for the low wettability of the electrodes during the adsorption of reagents by adding low concentrations of non-ionic detergents to the reagent solutions so as to facilitate the spreading of the solutions over the electrode surface. Even spreading is especially important during the localized immobilization of a reagent from a small volume of solution. For example, we have found that the addition of 0.005-0.04% Triton X-100® allows for the spreading of protein solutions over unetched surfaces without affecting the adsorption of the protein to the electrode and without disrupting the ability of a dielectric film applied on or adjacent to the electrode (preferably, a printed dielectric film with a thickness of 0.5-100 micrometers, or more preferably 2-30 micrometers, or most preferably 8-12 micrometers and having a sharply defined edge) to confine fluids to the electrode surface. Preferably, when non-ionic detergents such as Triton X-100 are used to facilitate spreading of capture reagents onto unetched screen-printed electrodes (i.e., so as to allow the immobilization of the capture reagents), the solutions containing the capture reagents are allowed to dry onto the electrode surface. It has been found that this drying step greatly improves the efficiency and reproducibility of the immobilization process.

Electrodes can be derivatized with chemical functional groups that can be used to attach other materials to them. Materials may be attached covalently to these functional groups, or they may be adsorbed non-covalently to derivatized or underivatized electrodes.

Electrodes may be prepared with chemical functional groups attached covalently to their surface. These chemical functional groups include but are not limited to COOH, OH, NH2, activated carboxyls (e.g., N-hydroxy succinimide (NHS)-esters), poly-(ethylene glycols), thiols, alkyl (($CH_2$)n) groups, and/or combinations thereof). Certain chemical functional groups (e.g., COOH, OH, NH2, SH, activated carboxyls) may be used to couple reagents to electrodes. For further reference to useful immobilization and bioconjugation techniques see G. Hermanson, A. Mallia and P. Smith, Immobilized Affinity Ligand Techniques (Academic Press, San Diego, 1992) and G. Hermanson, Bioconjugate Techniques (Academic Press, San Diego, 1996).

In specific embodiments, NHS-ester groups are used to attach other molecules or materials bearing a nucleophilic chemical functional group (e.g., an amine). In a specific embodiment, the nucleophilic chemical functional group is present on and/or in a biomolecule, either naturally and/or by chemical derivatization. Examples of suitable biomolecules include, but are not limited to, amino acids, proteins and functional fragments thereof, antibodies, binding fragments of antibodies, enzymes, nucleic acids, and combinations thereof. This is one of many such possible techniques and is generally applicable to the examples given here and many other analogous materials and/or biomolecules. In a preferred embodiment, reagents that may be used for ECL may be attached to the electrode via NHS-ester groups.

A reagent that can be used in an ECL assay can be attached to electrodes by covalent bonds (e.g., reaction with an NHS-ester), by reaction with an appropriate linker (vide supra), by non-specific binding, and/or by a combination thereof.

It may be desirable to control the extent of non-specific binding of materials to electrodes. Simply by way of non-limiting examples, it may be desirable to reduce or prevent the non-specific adsorption of proteins, antibodies, fragments of antibodies, cells, subcellular particles, viruses, serum and/or one or more of its components, ECL labels (e.g., RuII(bpy)3 and RuIII(bpy)3 derivatives), oxalates, trialkylamines, antigens, analytes, and/or combinations thereof). In another example, it may be desirable to enhance the binding of biomolecules.

One or more chemical moieties that reduce or prevent non-specific binding (also known as blocking groups) may be present in, on, or in proximity to an electrode. Such moieties, e.g., PEG moieties and/or charged residues (e.g., phosphates, ammonium ions), may be attached to or coated on the electrode. Examples of useful blocking reagents include proteins (e.g., serum albumins and immunoglobins), nucleic acids, polyethylene oxides, polypropylene oxides, block copolymers of polyethylene oxide and polypropylene oxide, polyethylene imines and detergents or surfactants (e.g., classes of non-ionic detergents/surfactants known by the trade names of Brij, Triton, Tween, Thesit, Lubrol, Genapol, Pluronic, Tetronic, and Span).

Materials used in electrodes may be treated with surfactants to reduce non-specific binding. For example, electrodes may be treated with surfactants and/or detergents that are well known to one of ordinary skill in the art (for example, the Tween series, Triton, Span, Brij). Solutions of PEGs and/or molecules which behave in similar fashion to PEG (e.g., oligo- or polysaccharides, other hydrophilic oligomers or polymers) ("Polyethylene glycol chemistry: Biotechnical and Biomedical Applications", Harris, J. M. Editor, 1992, Plenum Press) may be used instead of and/or in conjunction with surfactants and/or detergents. Undesirable non-specific adsorption of certain entities such as those listed above may be blocked by competitive non-specific adsorption of a blocking agent, e.g., by a protein such as bovine serum albumin (BSA) or immunoglobulin G (IgG). One may adsorb or covalently attach an assay reagent on an electrode and subsequently treat the electrode with a blocking agent so as to block remaining unoccupied sites on the surface.

In specific embodiments, it may be desirable to immobilize (by either covalent or non-covalent means) biomolecules or other media to carbon-containing materials, e.g., carbon black, fibrils, and/or carbon dispersed in another material. One may attach antibodies, fragments of antibodies, proteins, enzymes, enzyme substrates, inhibitors, cofactors, antigens, haptens, lipoproteins, liposaccharides, cells, sub-cellular components (e.g., organelles or membrane fragments), cell receptors, viruses, nucleic acids, antigens, lipids, glycoproteins, carbohydrates, peptides, amino acids, hormones, protein-binding ligands, pharmacological agents, and/or combinations thereof. It may also be desirable to attach non-biological entities such as, but not limited to polymers, elastomers, gels, coatings, ECL tags, redox active species (e.g., tripropylamine, oxalates), inorganic materials, chelating agents, linkers etc. A plurality of species may be co-adsorbed to form a mixed layer on the surface of an electrode.

Electrodes used in the multi-well assay plates of the invention are typically non-porous, however, in some applications it is advantageous to use porous electrodes (e.g., mats of carbon fibers or fibrils, sintered metals, and metals films deposited on filtration membranes, papers or other porous substrates. These applications include those that employ filtration of solutions through the electrode so as to: i) increase mass transport to the electrode surface (e.g., to increase the kinetics of binding of molecules in solution to molecules on the electrode surface); ii) capture particles on the electrode surface; and/or iii) remove liquid from the well.

Electrodes used in assay modules of the invention are advantageously able to induce luminescence from luminescent species. It is preferable that electrodes are comprised of materials that are compatible with biological media, impervious to the reagents typically encountered in luminescence measurements, and robust.

A working electrode may have one or more of the properties described above generally for electrodes. Preferably materials for working electrodes are materials able to induce electrochemiluminescence from Ruthenium-tris-bipyridine in the presence of tertiary alkyl amines (such as tripropyl amine). Examples of such preferred materials include graphene, alone or in combination with one or more of the following materials: platinum, gold, ITO, carbon, carbon-polymer composites, and conductive polymers. In one embodiment, the working electrode is made of a continuous conducting sheet or a film of one or more conducting materials. This sheet or film may be extruded, pressed or molded, and can be self supporting. In a preferred embodiment, the working electrode is made of a graphene-polymer composite. The composite may be comprised of graphene dispersed in a matrix (e.g., a polymer such as EVA, polystyrene, polyethylene, ABS). The working electrode may additionally comprise other conducting materials, for example, a conducting metal ink may be printed on the conducting composite.

In another embodiment, the working electrode is made of a conducting material deposited and/or patterned on a substrate (e.g., by printing, painting, coating, spin-coating, evaporation, chemical vapor deposition, electrolytic deposition, electroless deposition, photolithography and other electronics microfabrication techniques, etc.). In a specific embodiment, the working electrode comprises a conductive graphene ink printed on a polymeric support (e.g., by ink jet printing, laser printing, or, most preferably, by screen-printing). The working electrode may be a continuous film, it may be one or more discrete regions (e.g., patterns), or it may be a plurality of connected regions. The working electrode may additionally comprise other conducting materials, for example, an ink overlayer may be deposited over a conducting metal ink (e.g., a silver ink) underlayer, the underlayer being used to increase the conductivity of the film. It may be beneficial to print or deposit the overlayer in multiple layers so as to ensure that the underlayer is completely covered so that the underlayer doesn't interfere with subsequent processing steps or with ECL measurements (e.g., a preferred electrode material comprises two layers, preferably three layers, of ink over a layer of silver ink, the layers most preferably being deposited by screen printing). Alternatively, one or two layers of graphene may be used. For electrodes comprising one or more printed graphene ink layers over a printed silver ink layer, the silver layer has a thickness of, preferably, 2.5 microns to 25 microns, more preferably, 4-7 microns (or, alternatively, a thickness that produces a resistance of, preferably less than 2 ohms/square or, more preferably, 0.05-0.2 ohms/square) and the combined graphene layers have a thickness of, preferably, 2.5-75 microns or, more preferably, 6-25 microns (or, alternatively, a thickness that produces a resistance of, preferably less than 100 ohms/square or, more preferably, less than 30 ohms/square or, most preferably 20-30 ohms/square).

A counter electrode may have one or more of the properties described above generally for electrodes and for working electrodes. In one embodiment, the counter electrode is made of a continuous conducting sheet or a film of one or more conducting materials. This sheet or film may be extruded, pressed or molded, and can be self-supporting. In a specific embodiment, the counter electrode is made of a graphene-polymer composite. The composite may be comprised of conducting graphene particles dispersed in a matrix (e.g., a polymer such as EVA, polystyrene, polyethylene, ABS). The counter electrode may additionally comprise other conducting materials, for example, a conducting metal ink may be printed on the conducting composite.

In another embodiment, the counter electrode comprises a metal coating, film or foil. One specific embodiment of the invention is a multi-well plate having wells containing (preferably in two or more wells of the plate) working electrodes that comprise graphene dispersed in a matrix and counter electrodes comprising a metal coating, film or sheet or foil (specifically, comprising aluminum, stainless steel, nickel or silver). A foil counterelectrode may be self-supporting or may be supported on another material. It may also additionally comprise an adhesive material, a non-conducting layer and/or a backing material. The foil may have holes, advantageously in a pattern that corresponds to the pattern of wells in industry standard multi-well assay plates. Holes may be punched, drilled, burned, laser drilled, machined, etched or otherwise introduced by removing material from a continuous film, or, the film many be generated (e.g., molded) to incorporate holes. In a specific embodiment, the counter electrode is formed from a plastic sheet or support that is coated on one side with an aluminum film or foil and coated on the opposite side with an adhesive layer, preferably, having a removable backing strip.

In another embodiment, the counter electrode is made of a conducting material deposited and/or patterned on a substrate (as described above for the working electrode). In a specific embodiment, the counter electrode comprises a conducting graphene ink printed on a polymeric support. The counter electrode may be a continuous film, it may be one or more discrete regions (e.g., patterns), or it may be a plurality of connected regions. The counter electrode may additionally comprise other conducting materials, for example, a conducting metal ink (e.g., a silver ink) may be printed on the substrate and may be in contact with the conducting ink of the counter electrode.

The electrode compositions and surfaces described herein can be used in assay modules, e.g., multi-well assay plates and/or cartridges, configured for use in assays, preferably luminescence assays, more specifically electrode induced luminescence assays, e.g., electrochemiluminescence assays. The assay modules are suitable not only for ECL assays, but also suitable for fluorescence, chemiluminescence, bioluminescence, phosphorescence, optical transmittance, and electrochemical assays.

According to one specific embodiment of the invention, an assay module comprises a multi-well assay plate as described in U.S. application Ser. No. 10/185,274, incorporated herein by reference, e.g., including one or more (preferably two or more, 6 or more, 24 or more, 96 or more, 384 or more, 1536 or more or 9600 or more) assay wells, assay chambers and/or assay domains (e.g., discrete locations on a module surface where an assay reaction occurs and/or where an assay signal is emitted; typically an electrode surface, preferably a working electrode surface). According to a particular embodiment, the assay plate is a multi-well assay plate having a standard well configuration (e.g., 6 well, 24 well, 96 well, 384 well, 1536 well, 6144 well or 9600 well).

In order to enhance luminescence collection efficiency and/or reduce the size of the imaging surface and/or number of light detectors, the module is electrically addressable in sectors. That is, rather than measuring light from a single well, chamber, or assay domain at a time (which is time inefficient) or measuring light from the entire module (which reduces light collection efficiencies, requires multiple light detectors or requires the use of larger light detectors), the module and apparatus are configured to allow for the measurement of luminescence in portions of the assay module (preferably, more than one assay domain, well or chamber at a time, but less than all). Portions of the assay module can be segmented into sectors, where the terms "sector" or "sectors" when used in the context of a plate or module is used herein to refer to independently addressable groups of one or more (preferably two or more) jointly addressable assay wells, assay chambers or assay domains. For example, the sectors comprise one or more electrodes, more specifically, two or more jointly addressable (e.g., electrically connected) working electrodes.

One embodiment relates to an assay module (e.g., an assay plate or more specifically, a multi-well plate) for conducting luminescence assays (preferably electrode induced luminescence assays, more preferably electrochemiluminescence assays) comprising a substrate surface having a plurality of electrodes patterned thereon, wherein the plurality of electrodes are patterned so as to form independently addressable sectors comprising jointly addressable electrodes.

In one specific embodiment, the assay device is a cartridge, such as that described in copending U.S. application Ser. No. 12/959,952, filed Dec. 3, 2010, and U.S. application Ser. No. 10/744,726, filed Dec. 23, 2003, now U.S. Pat. No. 7,497,997, the disclosures of which are incorporated herein by reference. The assay cartridge may include a flow cell having a sample chamber, a detection chamber and an outlet, wherein the sample chamber, the detection chamber, and the outlet define a flow path through the flow cell, the detection chamber comprising a plurality of electrodes comprising the electrode compositions described herein.

Therefore, the invention includes an electrode comprising a multiplicity of graphene particles dispersed therein, wherein the electrode has one or more assay domains that include assay reagents, e.g., binding reagents, reaction substrates, or calibration reagents. In a specific embodiment, the assay reagents are binding reagents and the assay domains are referred to as binding domains. Assay domains can include assay reagents in dry, liquid or solid form and the reagents can be immobilized on the electrode surface. Assay domains can include binding reagents for one or more analytes in a sample and each assay domain can contain the same or different assay reagents. Assay domains can be formed by depositing reagents, e.g., by a variety of methods known in the art for depositing reagents, on specified locations on the surface of the electrode, e.g., the working electrode, or the reagents can be incorporated into the electrode composition. In a specific embodiment, the electrode includes a multiplicity of binding domains, and the binding reagents are selected from an antibody or fragment thereof, a nucleic acid, a receptor, an enzyme, or combinations thereof.

In a specific embodiment, the electrode surface includes a plurality of distinct binding domains supported on the surface, each domain containing a reagent capable of binding a component of a binding electrochemiluminescence assay, wherein at least two of the binding domains differ in their specificity for analytes of interest.

In a particular embodiment, the invention provides a multi-well plate comprising a plurality of wells, wherein two or more of said plurality of wells each comprise a working electrode surface and a counter electrode surface, wherein said working electrode surface and/or said counter electrode surface comprise screen printed graphene. In a specific embodiment, the working electrode surface comprises graphene. Optionally, the working electrode surface is formed by applying one or more layers of graphene onto a conductive layer comprising silver.

In another embodiment, the invention includes an assay module comprising a substrate having one or more fluid channels for introducing samples and/or assay reagents and one or more working electrode surfaces and one or more counter electrode surfaces on said substrate, wherein said working electrode comprises a graphene ink. In a specific embodiment, the working electrode surface and the counter electrode surface comprise a printed conductive material comprising graphene.

In a particular embodiment, the invention includes a multi-well plate comprising a plate top having plate top openings and a plate bottom mated to said plate top to define wells of said multi-well plate, said plate bottom comprising a substrate having a top surface with electrodes patterned thereon and a bottom surface with electrical contacts patterned thereon, wherein said electrodes and contacts are patterned to define two or more independently addressable sectors of two or more jointly addressable assay wells, each sector comprising two or more wells with: (a) jointly addressable working electrodes on said top surface of said substrate, wherein each of said working electrodes is electrically connected with each other and connected to at least a first of said electrical contacts; and (b) jointly addressable counter electrodes on said top surface of said substrate, wherein each of said counter electrodes is electrically connected with each other, but not with said working electrodes, and connected to at least a second of said electrical contacts, wherein said electrodes comprise graphene. In a specific embodiment, the electrodes patterned on the top surface are electrically connected to the electrical contacts patterned on the bottom surface, wherein the substrate further comprises one or more conductive through-holes electrically that provide said electrical connections between the electrodes patterned on the top surface and the electrical contacts patterned on the bottom surface.

EXAMPLES

Multi-well assay plates having screen printed graphene-modified electrodes were prepared as described in U.S. application Ser. No. 10/185,274, Example 6.1, the disclosure of which is incorporated herein by reference. Briefly, multi-layer plate bottoms were prepared by screen printing electrodes and electrical contacts on 0.005" thick Mylar polyester sheet. The Mylar sheet was first cut with a $CO_2$ laser so to form conductive through-holes as well as to form alignment holes that were used to align the plate bottom with the plate top. Electrical contacts were formed on the bottom of the Mylar sheet by screen printing an appropriately patterned silver ink layer (Acheson 479ss) and a graphene ink overlayer (X102 Vor-Ink™; provided by Vorbeck Materials, Jessup Md. 20794; http://www.vorbeck.com/graphene/vor-ink). A screen printed electrode using a graphite-carbon black ink, (Acheson PF407C, provided by Henkel North America, www.Henkelna.com) was also prepared for comparative purposes. The ink layer was dimensioned slightly larger (0.01 inches) than the silver ink layer to prevent exposure of the edge of the silver film. Working and counter electrodes were formed on the top of the Mylar film in a similar fashion except that three layers of ink were used to ensure that no silver remained exposed. The conductive through-holes were filled with conductive ink during these screen-printing steps. A dielectric ink was subsequently printed over the electrode layers so as to define the active exposed surface area of the working electrode. Typical registrational tolerances during the screen printing steps were +/−0.007-0.008 inches on the top side of the substrate and +/−0.010 inches on the bottom side. The separation between the printed counter and working electrode strips was kept at >0.010 inches to prevent the formation of short circuits. The working electrodes were conditioned for use in assays by treating the patterned plate bottoms for 5 min. with an oxygen plasma (2000 W, 200 mtorr) in a plasma chamber (Series B, Advanced Plasma Systems, St. Petersburg, Fla.) modified with large area flat electrodes.

Multi-well assay plates were assembled using the plate bottoms described above and injection molded plate tops. The dimensions of the plate tops met industry standards as established by the Society of Biomolecular Screening. The plate tops were made of black plastic (polystyrene loaded with black pigment). The bottom surfaces of the plate tops were contacted with die-cut double sided tape (1 mil PET coated on each side with 2 mil of acrylic pressure sensitive adhesive) so as to allow for sealing of the plate tops to the plate bottoms. The tape was cut to form holes that were slightly oversized relative to the holes in the plate tops. The plate bottoms were fixed (using the laser cut alignment holes) onto alignment pins on an X-Y table. The plate bottoms were optically aligned to the plate tops and then sealed together using a pneumatic press (400 pounds, 4 s). Alignment was carried out sufficiently accurately so that the exposed working electrodes were centered within the wells (+/−0.008 inches).

Voltammetry was measured using the graphene-modified electrodes of various buffer components in three different electrochemiluminescence (ECL) read buffers, buffer (S): 200 mM potassium phosphate monobasic, 0.1% Triton X-100, 100 mM tripropylamine (TPA), pH 7.5; buffer (T): 200 mM Trizma HCl, 50 mM potassium chloride, 0.1% Triton X-100, 125 mM TPA, pH 7.8; buffer (P): 80 mM potassium phosphate monobasic, 0.1% Triton X-100, 20 mM Pipes sodium, 0.02% Kathon, pH 7.5. Six different solutions were run for each read buffer measurement: (i) base electrolyte solution, (ii) base electrolyte solution with 40 nM TAG (available from Meso Scale Discovery, Rockville, Md.), (iii) base electrolyte solution with 0.01% Triton X-100, (iv) base electrolyte solution with 0.1% Triton X-100 and 40 nM TAG, (v) completed 1×ECL read buffer, and (vi) completed 1× read buffer with 40 nM TAG. Each set of six solutions for a read buffer were measured on one plate, with each solution pipetted into one sector of a plate so that the voltammetry data for each solution could be assessed. The plates were filled, allowed to set covered for at least 15 minutes, and then the voltammetry was measured.

Figure 1B:
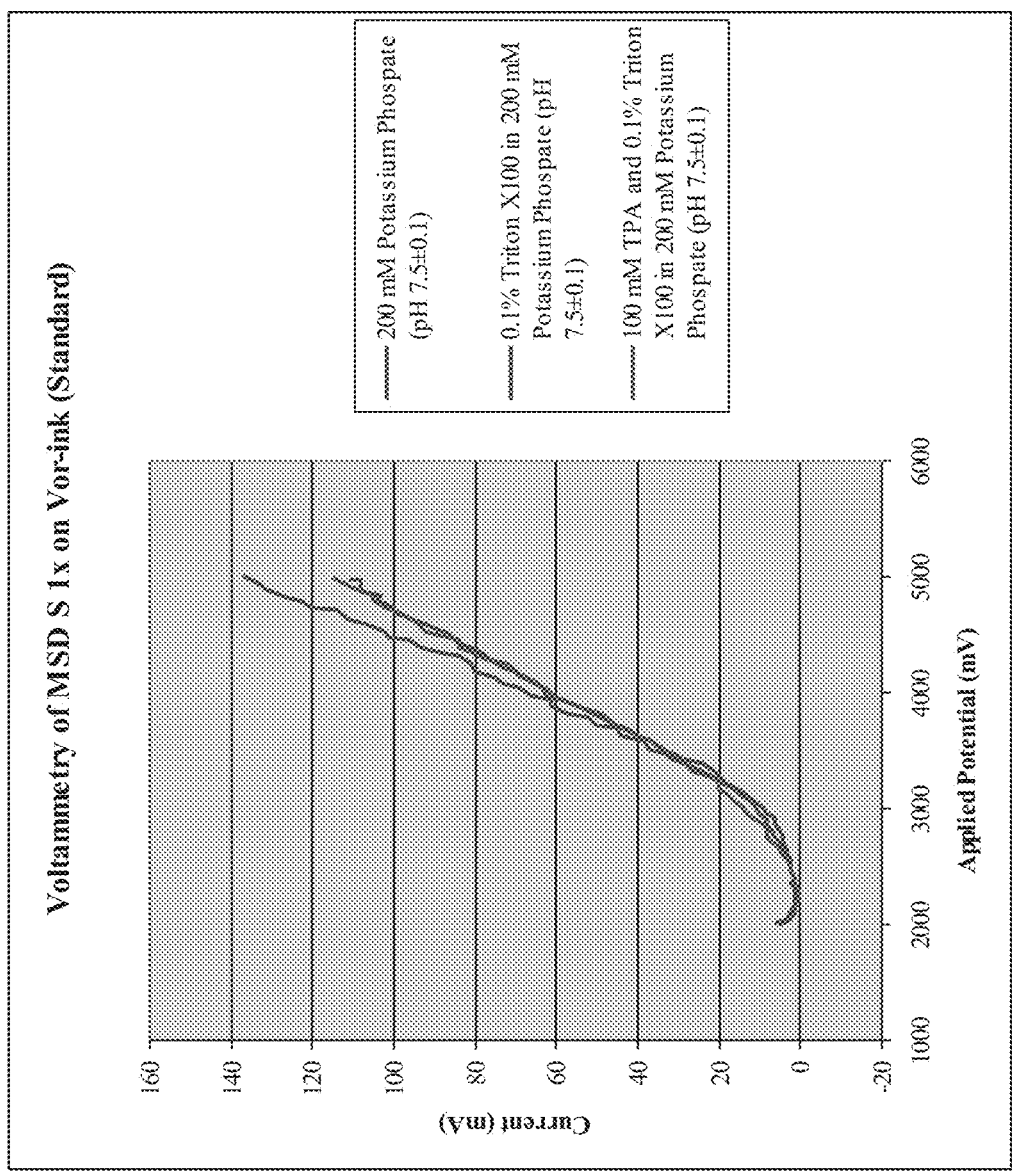
Figure 2A:
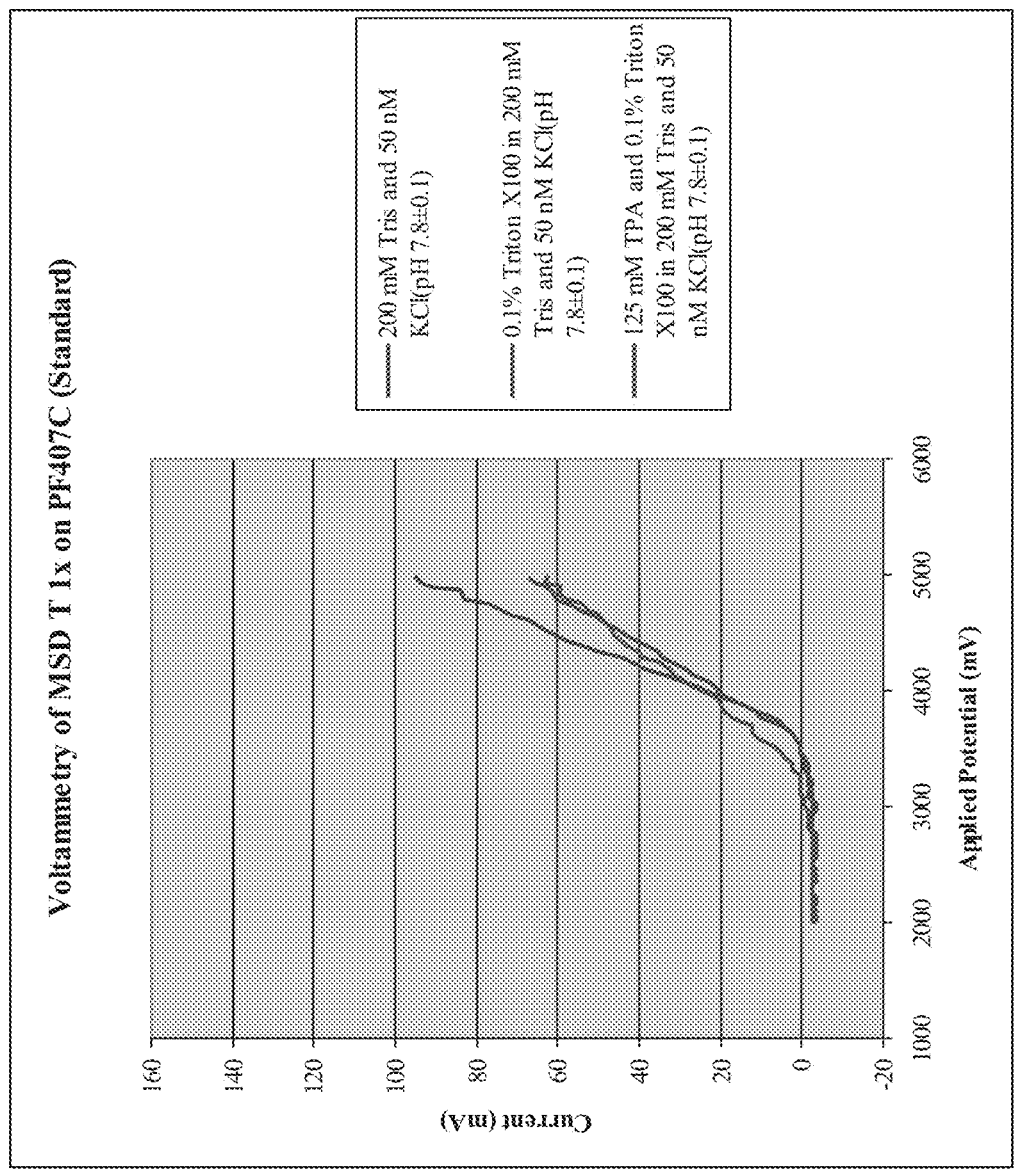
FIGS. 2(a)-(b) are graphs showing the voltammetry of T buffer using PF407C (panel (a)) and Vor-ink X102 (panel (b)), respectively.
Figure 2B:
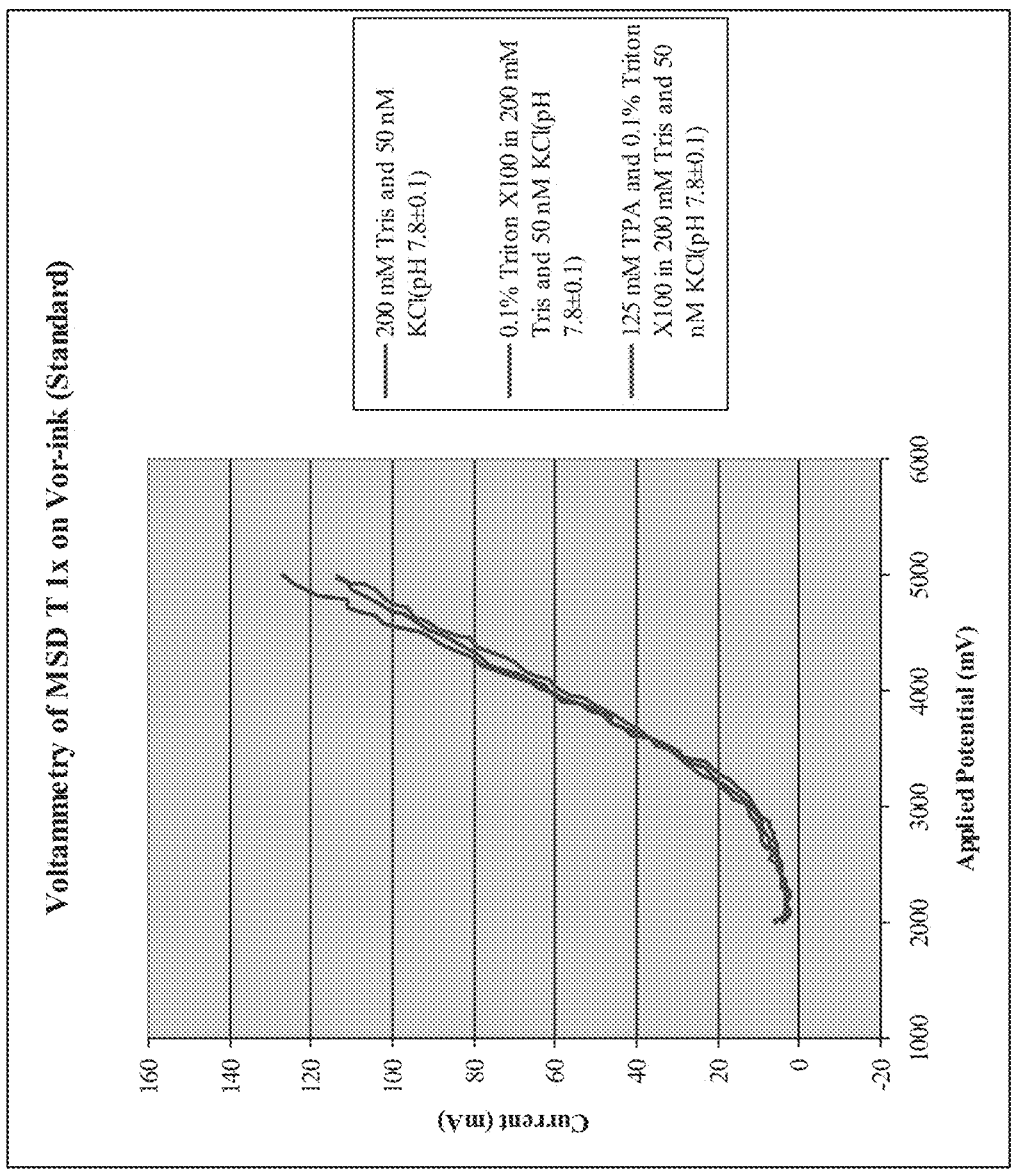
Figure 3A:
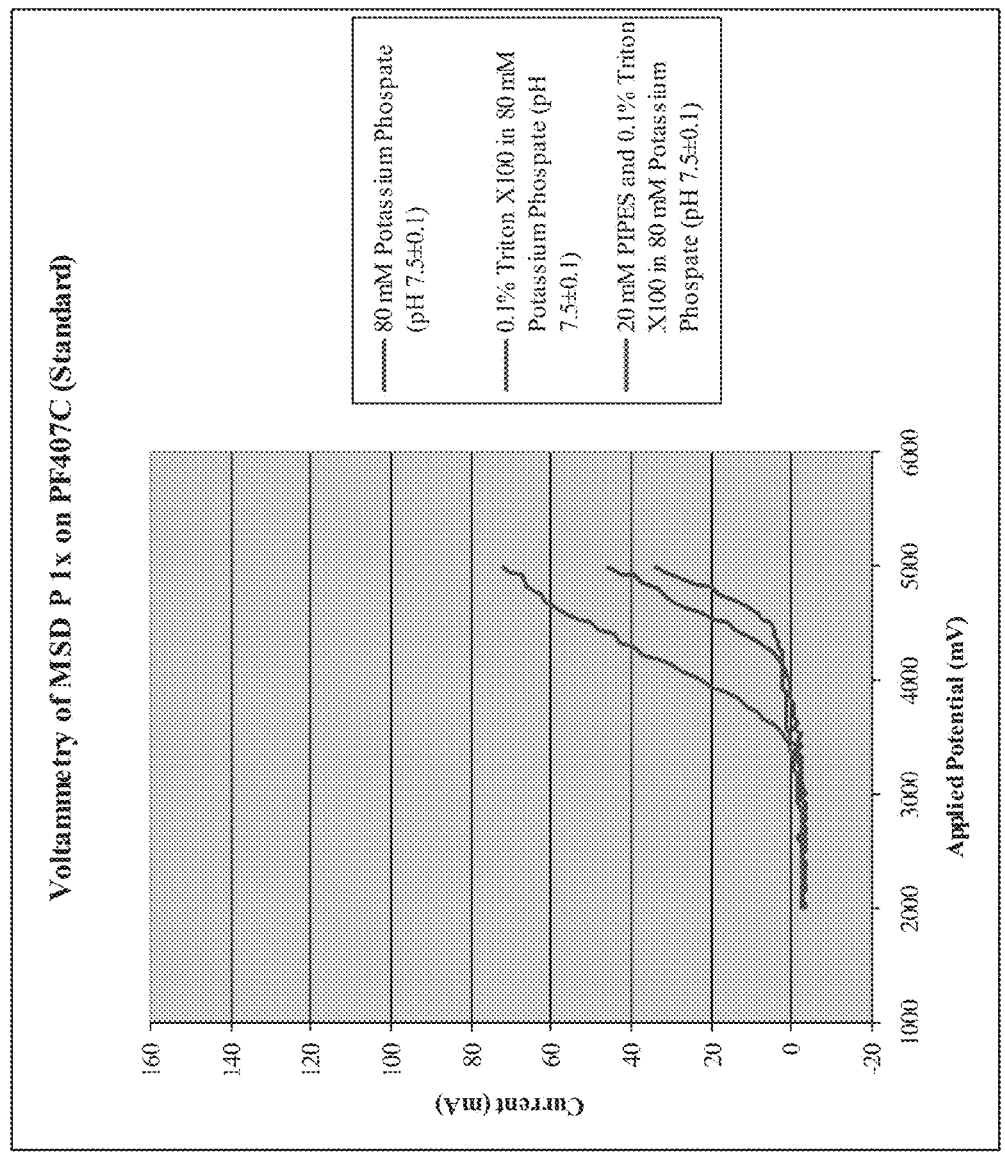
FIGS. 3(a)-(b) are graphs showing the voltammetry of P buffer using PF407C (panel (a)) and Vor-ink X102 (panel (b)), respectively.
Figure 3B:
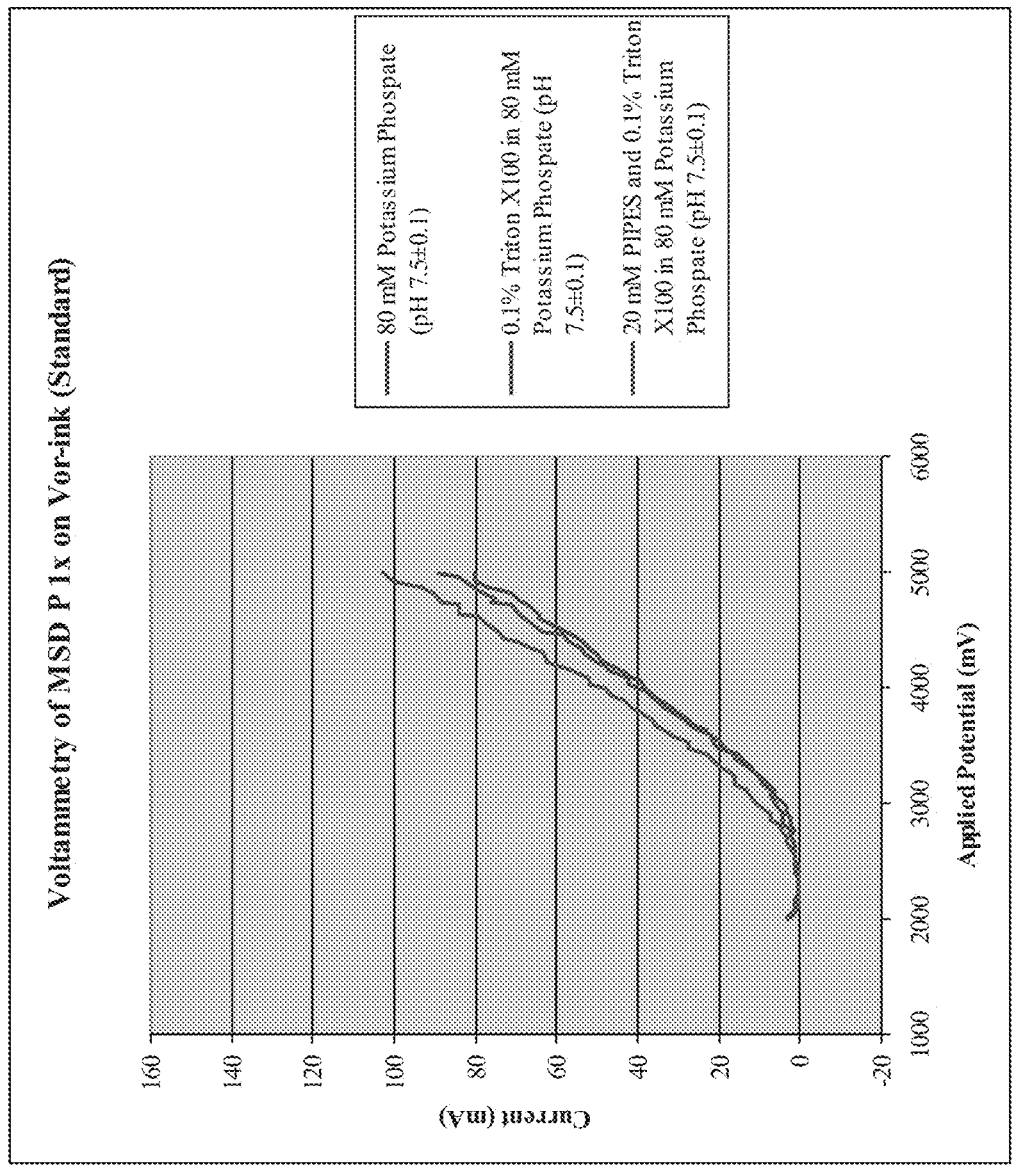

Voltammagrams are shown in FIGS. 1-3, for buffers (S), (T), and (P), respectively for plates that include Vor-ink vs. plates including PF407C ink. FIGS. 1(a) and 1(b) are voltammagrams for PF407C and Vor-ink, respectively, in buffer (S), FIGS. 2(a) and 2(b) are voltammagrams for PF407C and Vor-ink, respectively, in buffer (T), and FIGS. 3(a) and 3(b) are voltammagrams for PF407C and Vor-ink, respectively, in buffer (P).

Figure 6:
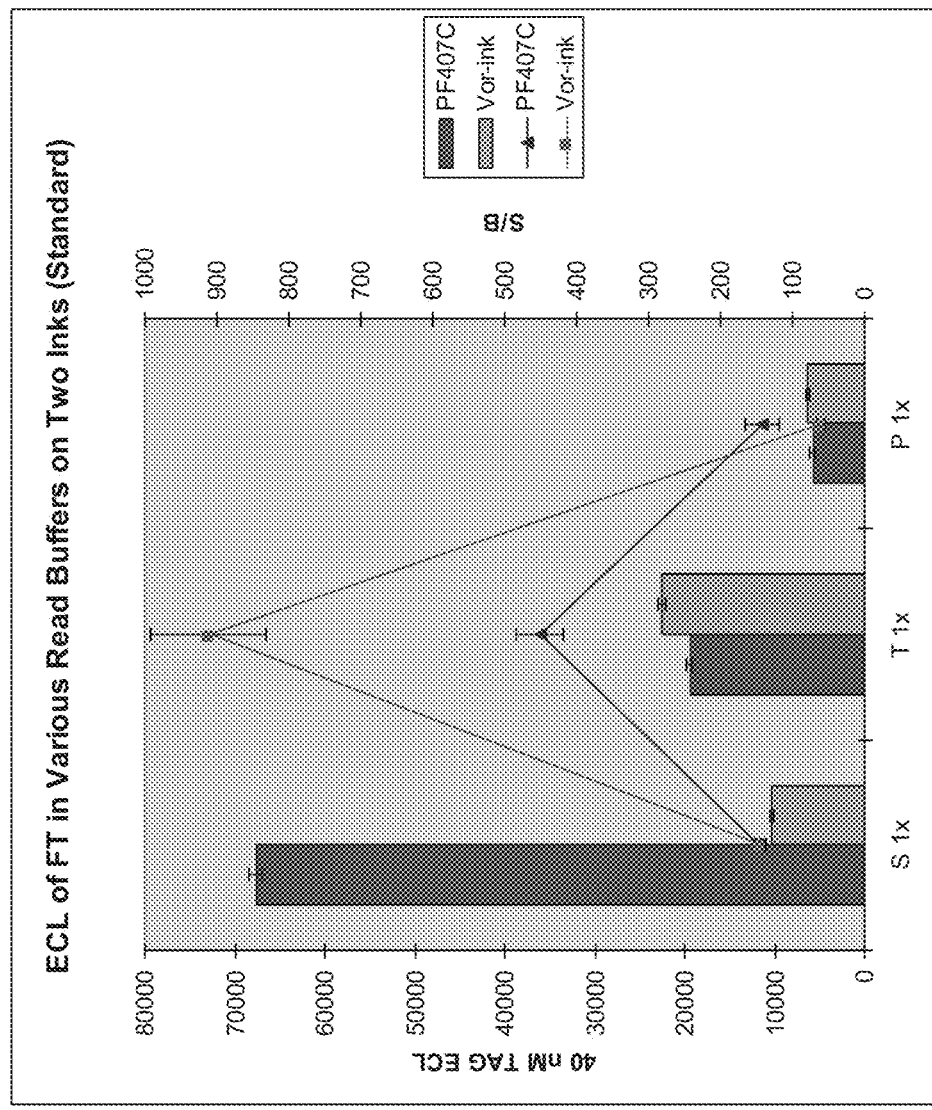
FIG. 6 shows a plot of FT signals and S/B ratios for PF407C and X102 ink formulations.

ECL images were also reviewed for each electrode surface. ECL signals (low signals) were obtained from solutions without a co-reactant (e.g., TPA). No low level ECL signals were observed without co-reactant on Vor-ink. ECL images are shown in FIGS. 4-5, wherein FIGS. 4(a)-(l) are ECL images for electrodes comprising PF407C, and FIGS. 5(a)-(f) are ECL images for electrodes comprising Vor-ink. ECL images generated using buffer (P) were generally non-uniform, with more ECL near the counter electrodes and highly sensitive to surface defects. In addition, the mean, standard deviation (% CV) were calculated for each solution (n=16 wells), as well as the signal-to-background ratios (S/B) (40 nM TAG/ECL Read Buffer), and error in these ratios were calculated from the measured standard deviations. A plot of FT signals and S/B ratios was is shown in FIG. 6 for both ink formulations. The data are provided below in Table 1:

|  | PF407C | | | Vor-ink | | |
| --- | --- | --- | --- | --- | --- | --- |
|  | ECL | StDev | % CV | ECL | StDev | % CV |
| S 1x | 458 | 6 | 1.4% | 71 | 3 | 4.9% |
| 40 nM TAG in S 1x | 67649 | 673 | 1.0% | 10268 | 176 | 1.7% |
| S/B | 148 | 2 | 1.7% | 145 | 8 | 5.2% |
| T 1x | 43 | 3 | 7.1% | 25 | 2 | 8.7% |
| 40 nM TAG in T 1x | 19421 | 303 | 1.6% | 22623 | 417 | 1.8% |
| S/B | 451 | 33 | 7.2% | 912 | 81 | 8.9% |
| P 1x | 40 | 6 | 16.1% | 104 | 5 | 4.8% |
| 40 nM TAG in P 1x | 5750 | 275 | 4.8% | 6368 | 234 | 3.7% |
| S/B | 143 | 24 | 16.8% | 61 | 4 | 6.0% |

The ECL signal from buffer (S) was sensitive to the ink composition, whereas the S/B was not as sensitive to composition. The ECL signal from buffer (T) showed a 16% increase from TAG and a decrease from read buffer with Vor-ink, yielding an increase in S/B. And the ECL signal from buffer (P) increased for both TAG and read buffer on Vor-ink surfaces but there was a decrease in the S/B on Vor-ink.

In summary, the impact of carbon ink on voltammetry and ECL was measuring using buffers (S), (T), and (P). The current was measured for the base electrolyte solutions, with the addition of Triton X-100, and the completed buffer at the pH specified for the final solution. It was found that the current was higher using the graphene ink formulation relative to that observed for graphite-carbon black ink formulations. Without wishing to be bound by any theory, the increase in current is likely attributable to water and/or graphene oxidation. The ECL magnitude in buffer (S) was found to be sensitive to the ink formulation and notably lower using graphene ink formulation, the TAG ECL magnitude in buffer (T) was slightly higher and with a slightly lower read buffer ECL signal the S/B was higher on the graphene ink surface relative to the carbon ink surface, and both TAG and read buffer signals increased for buffer (P) on graphene surfaces with a decrease in S/B on graphene.

The present invention is not to be limited in scope by the specific embodiments described herein. Indeed, various modifications of the method in addition to those described herein will become apparent to those skilled in the art from the foregoing description and accompanying figures. Such modifications are intended to fall within the scope of the claims. Various publications are cited herein, the disclosures of which are incorporated by reference in their entireties.

The invention claimed is:

1. An assay electrode comprising:
a composite containing a matrix, a thermoplastic polymer, and a multiplicity of graphene particles dispersed therein, said assay electrode having a binding domain containing a binding reagent, wherein said binding reagent is immobilized on a surface of said assay electrode,
wherein the thermoplastic polymer is selected from the group consisting of a cellulosic resin, an epoxy resin and a UV-curable resin, and wherein a ratio of thermoplastic polymer to graphene particles is between 0.5 kg/kg to 1.2 kg/kg, and
wherein the composite further comprises a glycol drying-retarder agent selected from the group consisting of dibutyl phthalate; diocyl phthalate; tributyl phosphate; 1,3 butylene glycol, and combinations thereof.

2. An assay electrode as recited in claim 1, wherein said assay electrode includes a multiplicity of binding domains.

3. An assay electrode as recited in claim 1, wherein said binding reagent is an antibody or fragment thereof, a nucleic acid, a receptor or an enzyme.

4. An assay electrode of claim 1 wherein said multiplicity of graphene particles comprise a mixture of different graphene formulations.

5. An assay electrode as recited in claim 1, wherein the thermoplastic polymer is present in the composite at about 0.25% to about 20% by weight.

6. An assay electrode as recited in claim 1, wherein the composite further comprises a polymer.

7. An assay electrode as recited in claim 6, wherein the polymer is present in the composite at about 10% to about 70% by weight.

8. An assay electrode as recited in claim 6, wherein the polymer is selected from the group consisting of polyurethane, acrylic, polyester and vinyl resin polymers.

9. An assay electrode as recited in claim 1, wherein the glycol drying-retarder agent is present in the composite at about 2% to about 20% by weight.

10. An assay electrode as recited in claim 1, wherein the graphene particles are exfoliated particles of a graphene sheet, wherein the graphene sheet has a surface area of from about 300 $m^2/g$ to about 2630 $m^2/g$.

11. An assay electrode as recited in claim 1, wherein the graphene particles are exfoliated particles of a graphene sheet, wherein the graphene sheet has a bulk density of about 0.1 $kg/m^3$ to about 40 $kg/m^3$.

12. An assay electrode as recited in claim 1, wherein the graphene particles are exfoliated particles of a graphene sheet, wherein the graphene sheet has an overall carbon to oxygen molar ratio (C:O ratio) of at least about 3:2.

13. An assay electrode as recited in claim 1, wherein the graphene particles have an average particle size of about 1 micron to about 50 microns.

14. An assay electrode as recited in claim 1, wherein the composite has a viscosity of about 8,000 cP at 30° C. to about 80,000 cP at 30° C.

15. An assay electrode as recited in claim 1, wherein the assay electrode comprises two or more layers of the composite.

16. An assay electrode as recited in claim 15, wherein a thickness of the two or more layers of the composite is 2.5 microns to 75 microns.

17. An assay electrode as recited in claim 15, wherein a resistance of the two or more layers is less than 100 ohms/square.

18. An assay electrode as recited in claim 1, wherein the assay electrode further comprises an electrically conductive component.

19. An assay electrode as recited in claim 18, wherein the electrically conductive component is selected from the group consisting of metals, metal alloys, conductive metal oxides, polymers, carbonaceous materials other than graphene sheets, and metal-coated materials.

20. An assay electrode as recited in claim 1, wherein the assay electrode further comprises a material selected from the group consisting of a semiconducting material and a semi-conducting film.

21. An assay electrode as recited in claim 20, wherein the material is selected from the group consisting of silicon, germanium, indium tin oxide, and antimony tin oxide.

22. An assay electrode as recited in claim 1, wherein the assay electrode is substantially free of silicone-based materials.

23. An assay electrode as recited in claim 1, wherein the assay electrode is supported on a material selected from a film, a plastic sheet, an adhesive film, paper, a backing, a mesh, a felt, a fibrous material, a gel, a metal, a ceramic, a glass, an elastomer, a liquid, a tape, an adhesive, an other electrode, and a dielectric material.

24. An assay electrode as recited in claim 1, wherein the assay electrode comprises a porous material.

25. An assay electrode as recited in claim 24, wherein the porous material is selected from a mat of carbon fibers, a mat of carbon fibrils, a sintered metal, a metal films deposited on a filtration membrane, and a paper.

26. An assay electrode as recited in claim 1, wherein the assay electrode further comprises a material selected from the group consisting of a metal coating, a metal film, and a metal foil.

27. An assay electrode as recited in claim 1, wherein the ratio of thermoplastic polymer to graphene particles is between 0.9 kg/kg to 1.1 kg/kg.

28. An assay electrode as recited in claim 1, wherein the thermoplastic polymer is selected from the group consisting of polyethyloxyazoline, polyvinyl pyrrolidone, and polyacrylamide.

29. An assay electrode as recited in claim 25, wherein the porous material is selected from a sintered metal and a metal film deposited on a filtration membrane.

* * * * *